United States Patent [19]

Schwender et al.

[11] 4,116,961

[45] Sep. 26, 1978

[54] 1,2-BENZOXATHIIN-2,2,-DIOXIDES

[75] Inventors: Charles F. Schwender, Lebanon; Brooks R. Sunday, Hackettstown, both of N.J.

[73] Assignee: Warner-Lambert Company, Morris Plains, N.J.

[21] Appl. No.: 771,502

[22] Filed: Feb. 24, 1977

[51] Int. Cl.$^2$ .................. C07D 411/04; C07D 327/06
[52] U.S. Cl. ........................... 260/293.57; 260/327 S; 260/456 P
[58] Field of Search ....................... 260/327 S, 293.57

[56] References Cited

U.S. PATENT DOCUMENTS

| | | | |
|---|---|---|---|
| 3,367,864 | 2/1968 | Elliott et al. | 260/327 S |
| 4,007,203 | 2/1977 | Zinnes et al. | 260/293.57 |

FOREIGN PATENT DOCUMENTS 1,238,158  7/1971  United Kingdom ................ 260/327 S

OTHER PUBLICATIONS

Chemical Abstracts, 79, 105159t (1973) [Clancy, J. M. et al., *Int. J. Sulfur Chem.*, Part A 1972, 2(4), 249–255].

*Primary Examiner*—Henry R. Jiles
*Assistant Examiner*—Richard A. Schwartz
*Attorney, Agent, or Firm*—Albert H. Graddis; Frank S. Chow; George M. Yahwak

[57] ABSTRACT

Disclosed are substituted 1,2-benzoxathin-2,2-dioxide, and methods for their manufacture. These compounds show antiinflammatory activity.

14 Claims, No Drawings

1,2-BENZOXATHIIN-2,2,-DIOXIDES

The present invention relates to compounds of the formula:

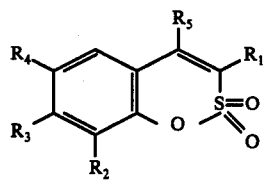

wherein $R_1$ may be carboxamido ($CONH_2$) wherein the nitrogen atom may be further mono- substituted by either a straight, branched, or cyclic alkyl chain of between 1 and 6 carbon atoms in length, or aryl such as phenyl which may also be substituted by either halogen or a lower alkyl of 1 to 4 carbon atoms in length; wherein $R_2$, $R_3$, and $R_4$ together or separately may be halogen such as chlorine or bromine, lower alkyl of 1 to 4 carbon atoms, aryl such as phenyl, or wherein $R_3$ and $R_4$ may be joined together in the form of a ring such as naphthyl or tetrahydronaphthyl; and wherein $R_5$ is hydroxy, lower alkoxy of 1 to 4 carbon atoms, or $NR_6R_7$ wherein $R_6$ and $R_7$ are both lower alkyl of 1 to 4 carbon atoms or together with the nitrogen atom to which they are attached form a cyclicamino such as piperidino, pyrrolidino, morpholine or thiomorpholino.

Also, chelate salts of the above compounds are also included for all pharmaceutically acceptable multivalent metals such as calcium, copper and magnesium.

A key intermediate (II) in the synthesis of the claimed compounds of this invention is prepared via a novel base-catalyzed cyclization of 2-methylsulfonate-benzoic acid ester (I) to form the benzoxathiin-2,2-dioxide ring system (II). This ring system has not previously been synthesized by this method.

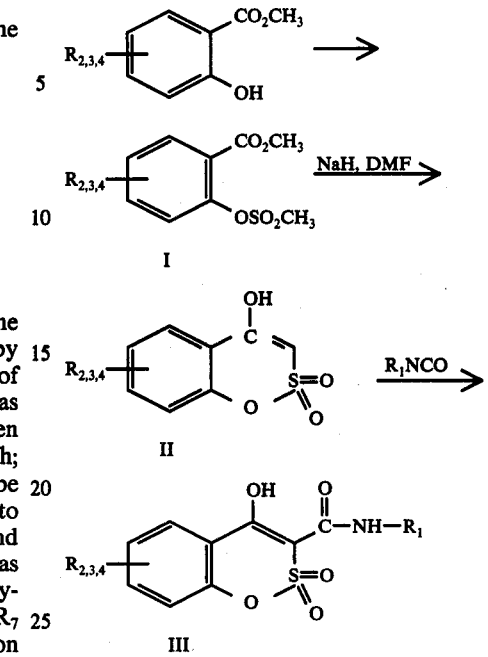

The appropriately-substituted salicylate ester is converted to the methylsulfonate with methanesulfonyl chloride and $Et_3N$ in ether or pyridine. Cyclization of I to form the oxathiin ring is accomplished by heating the sulfonate in DMF in the presence of NaH. Condensation of II and a substituted isocyanate in DMF and NaH gives the desired carboxamido product III.

The corresponding analogs where $R_5 = NR_1R_1$ as a cyclic amino substitution are prepared from the 4-hydroxy ($R_5 = OH$) intermediate using $TiCl_4$, an amine such as piperidine and an inert solvent such as benzene. The physical properties of the compounds prepared are in the table below:

| $R_1$ | $R_2$ | $R_3$ | $R_4$ | $R_5$ | mp °C |
|---|---|---|---|---|---|
| $CONHC_6H_5$ | H | H | Br | OH | 223–226 |
| H | H | H | H | —N(piperidino) | 187–189 |
| $CONHC_6H_5$ | $C_6H_5$ | H | H | OH | 181–183 |
| $CONHC_6H_5$ | H | H | H | OH | 175–178 |
| $CONHC_4H_9n$ | H | H | H | OH | 93–96 |
| $CONHC_6H_5$ | H | —CH=CH—CH=CH— | | OH | 257–260 |
| H | H | H | Br | OH | 129–131 |
| H | H | —CH=CH—CH=CH— | | OH | 190–193 |
| H | $C_6H_5$ | H | H | OH | 141–144 | and intermediates

-continued

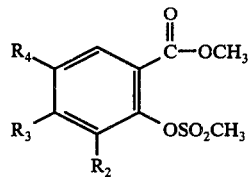

| $R_2$ | $R_3$ | $R_4$ | mp °C |
|---|---|---|---|
| H | —CH=CH—CH=CH— | | 100–103 |
| $C_6H_5$ | H | H | 120–124 |
| H | H | Br | oil |

In order to obtain a greater understanding of our invention, the following examples are given:

EXAMPLE 1

Methyl 2-methanesulfonyl-3-phenylbenzoate

An ethereal solution (1 liter) containing 50.0 g (0.22 mol) of methyl 2-hydroxy-3-phenylbenzoate, 0.25 mole of methanesulfonyl chloride and 0.25 mole of $Et_3N$ was allowed to react at room temperature for 18 hours. The reaction mixture was washed with 1 N NaOH (1 × 1 liter) and $H_2O$ (1 × 500 ml). After drying with $MgSO_4$ the ether solution was evaporated to give a yellow solid; yield 61.9 g (91.7%), mp. 101°–115°. Recrystallization of the crude product from benzene-hexane gave the analytical sample, mp. 120°–124°.

EXAMPLE 2

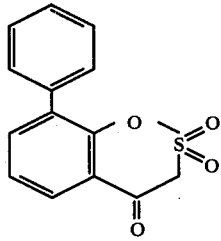

4-Hydroxy-8-phenyl-1,2-benzoxathiin-2,2-dioxide

A mixture of 39.0 g (127 mmol) of methyl 2-methanesulfonyl-3-phenylbenzoate, 140 mmole of NaH and 150 ml of dry DMF was heated at 70° for 2.5 hours. The reaction mixture was poured into ice-$H_2O$ (1 liter), acidified with 6 N HCl and extracted with $Et_2O$ (3 + 1 liter). The ether extract was dried ($MgSO_4$) and evaporated to give the crude product as an oil which crystallized from a 2-PrOH/hexane mixture; yield 20.5 g (58.9%), mp. 100°–110°. The analytical sample was obtained by recrystallization from EtOH, mp. 141°–144°.

EXAMPLE 3

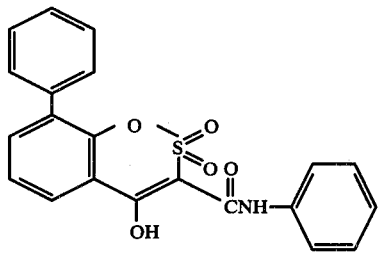

4-Hydroxy-8-phenyl-1,2-benzoxathiin-3-carboxanilide

Phenylisocyanate (20.5 mmol) was added to a cooled DMF solution (25 ml) containing 20.5 mmol of NaH and 5.0 g (18.3 mmol) of 4-hydroxy-8-phenyl-1,2-benzoxathiin-2,2-dioxide. The resultant mixture was heated at 75° for 2.5 hours. The mixture was cooled, poured into ice-$H_2O$ (100 ml) and acidified with HCl. The resultant precipitate was collected by filtration and gave 6.70 g (93.3%) of the expected product, mp. 175°. The crude product was purified by recrystallization from 2-PrOH/hexane to give the analytical sample, mp. 181°–183°.

EXAMPLE 4

4-Piperidinobenzoxathiin-2,2-dioxide

To a cooled benzene solution (250 ml) containing 60 mmol of piperidine and 1.98 g (10 mmol) of 4-hydroxybenzoxathiin was added 10 mmol of $TiCl_4$ in 25 ml of benzene. The resultant mixture was allowed to react at room temperature for 96 hours. The mixture was evaporated in vacuo to a residual solid which was extracted with hot acetone. Evaporation of the acetone extract gave the crude product as a solid which was immediately recrystallized from benzene-hexane to give the analyrical sample, yield, 2.02 g (76.2%), mp. 187°–189°.

The compounds of this structure are useful as antiinflammatory agents. When administered intraperitoneally to rats at a dose of 100 mg/kg, they are able to cause a reduction in swelling of the paw induced by an infection of an irritant such as carrageenin.

We claim:

1. A compound of the formula:

wherein $R_1$ is $N(R_6)$ carbamoyl wherein $R_6$ is selected from the group consisting of phenyl or lower alkyl of 1 to 6 carbon atoms; wherein $R_2$ is selected from the grop consisting of hydrogen and phenyl; wherein $R_3$ is hydrogen; wherein $R_4$ is hydrogen or halogen; and wherein $R_5$ is hydroxyl, and the pharmaceutically acceptable chelate salts thereof.

2. A compound according to claim 1 wherein $R_1$ is —CONHC$_6$H$_5$.

3. The compound of claim 2 which is 6-bromo-4-hydroxy-1,2-benzoxathiin-3-carboxanilide 2,2-dioxide.

4. The compound of claim 2 which is 4-hydroxy-N,8-diphenyl-1,2-benzoxathiin-3-carboxamide 2,2-dioxide.

5. The compound of claim 2 which is 4-hydroxy-N-phenyl-1,2-benzoxathiin-3-carboxamide 2,2-dioxide.

6. The compound of claim 1 which is N-butyl-4-hydroxy-1,2-benzoxathiin-3-carboxamide 2,2-dioxide.

7. A compound of the formula:

wherein $R_1$ is $N(R_6)$ carbamoyl wherein $R_6$ is selected from the group consisting of phenyl or lower alkyl of 1 to 6 carbon atoms; wherein $R_2$ is selected from the group consisting of hydrogen and phenyl; wherein $R_3$ is hydrogen; wherein $R_4$ is selected from the group consisting of hydrogen or halogen; and the pharmaceutically acceptable chelate salts thereof.

8. The compound of claim 7 which is 8-phenyl-1,2-benzoxathiin-4(3H)-one 2,2-dioxide.

9. The compound of claim 7 which is 6-bromo-1,2-benzoxathiin-4(3H)-one 2,2-dioxide.

10. A compound of the formula wherein $R_1$ is —H or —CONHC$_6$H$_5$; $R_2$ is hydrogen; $R_3$ and $R_4$ together are —CH=CH—CH=CH—; and $R_5$ is hydroxyl.

11. The compound of claim 10 which is 4-hydroxynaphth[2,3-e][1,2]oxathiin-3-carboxanilide 2,2-dioxide.

12. A compound of the formula:

wherein $R_1$ is hydrogen or —CONHC$_6$H$_5$; $R_2$ is hydrogen; and $R_3$ and $R_4$ taken together are —CH=CH—CH=CH—.

13. Naphth[2,3-e][1,2]oxathiin-4(3H)one 2,2-dioxide.

14. 4-piperidinobenzoxathiin-2,2-dioxide.

* * * * *